(12) United States Patent
Ueda et al.

(10) Patent No.: US 8,853,464 B2
(45) Date of Patent: Oct. 7, 2014

(54) METHOD OF PRODUCING REDUCED COENZYME $Q_{10}$ CRYSTALS WITH EXCELLENT HANDLING PROPERTIES

(75) Inventors: Takahiro Ueda, Hyogo (JP); Shiro Kitamura, Hyogo (JP); Yasuyoshi Ueda, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 13/176,479

(22) Filed: Jul. 5, 2011

(65) Prior Publication Data

US 2011/0263906 A1 Oct. 27, 2011

Related U.S. Application Data

(63) Continuation of application No. 10/483,603, filed as application No. PCT/JP02/07144 on Jul. 15, 2002, now Pat. No. 8,003,828.

(30) Foreign Application Priority Data

Jul. 13, 2001 (JP) ................................. 2001-214474
Apr. 17, 2002 (JP) ................................. 2002-114872

(51) Int. Cl.
*C07C 41/40* (2006.01)

(52) U.S. Cl.
CPC ..................................... *C07C 41/40* (2013.01)
USPC .......................................... 568/651; 568/652

(58) Field of Classification Search
None
See application file for complete search history.

(56) References Cited

U.S. PATENT DOCUMENTS

| | | | | |
|---|---|---|---|---|
| 3,066,080 | A * | 11/1962 | Folkers et al. | ............... 435/133 |
| 3,068,295 | A | 12/1962 | Folkers at al. | |
| 3,162,654 | A | 12/1964 | Crane at al. | |
| 3,497,522 | A | 2/1970 | Imada et al. | |
| 4,308,110 | A | 12/1981 | Hosaka et al. | |
| 5,672,725 | A | 9/1997 | Polis | |
| 6,184,255 | B1 | 2/2001 | Mae et al. | |

FOREIGN PATENT DOCUMENTS

| | | | |
|---|---|---|---|
| CN | 1298942 | A | 6/2001 |
| GB | 947643 | A | 1/1964 |
| JP | 52-72884 | A | 6/1977 |
| JP | 53-133687 | A | 11/1978 |
| JP | 54-119424 | A | 9/1979 |
| JP | 54 140793 | A | 11/1979 |
| JP | 56 144091 | A | 11/1981 |
| JP | 57-070834 | A | 5/1982 |
| JP | 6075294 | A | 4/1985 |
| WO | WO-9617626 | A2 | 6/1996 |
| WO | WO-9804512 | A1 | 2/1998 |

OTHER PUBLICATIONS

Mersmann (Crystallization Technology handbook, 2001, p. 553).*
Supplementary European Search Report from Application No. EP 0274 6037, Dec. 20, 2005, 4 pages.
International Search Report From Corresponding International Application No. PCT/JP02/07144, Dated Oct. 21, 2002, 1 Page.
Patent Cooperation Treaty International Preliminary Examination Report (PCT Article 36 and Rule 70), From Corresponding International Application No. PCT/JP02/07144, Dated May 28, 2004, 4 Pages.
Amanoo Pharm KK, Derwent abstract of JP 56144091, published Nov. 1981.
English translation of JP 54-119424, published Sep. 1979.
Office Action for counterpart CN Application No. 200610087651.4, which was received on Jun. 4, 2007.
Cheng-Hong-Ming et al., "Preparation of C- and H-Methoxyl-labelled Forms of Ubiquinone by Photochemical O-Demethylation and Subsequent Remethylation," Journal of Labelled Compounds, vol. VI, No. 1, pp. 66-75 (XP008057436). Jan.-Mar. 1970.
Office Action for counterpart EP Application No. 02746037.7, which was received on Jun. 25, 2007.
Foti, M. et al., The Surprisingly High Reactivity of Phenoxy Radicals, J. Am. Chem. Soc., vol. 116, No. 21, 1994, pp. 9440-9447.
Moyers et al., Crystal-Size Distribution and its Interaction with Crystallizer Design, A.I.Ch.E., vol. 19, No. 6, Nov. 1973, pp. 1089-1104.
Kirk-Othmer Encyclopedia of Chemical Technology, Crystallization, vol. 8, 2001, pp. 95-147.
Ajinomoto Co., English translation of JP 54-119424, published Sep. 1979.
Patent Cooperation Treaty International Preliminary Examination Report (PCT Article 36 and Rule 70), From Corresponding International Application No. PCT/JP02/07144, Dated May 28, 2003 4 Pages.

* cited by examiner

*Primary Examiner* — Rosalynd Keys
(74) *Attorney, Agent, or Firm* — Novak Druce Connolly Bove + Quigg LLP

(57) ABSTRACT

The present invention provides a method of producing reduced coenzyme $Q_{10}$ crystals suitable for commercial scale production thereof.
According to a method of the present invention of producing a reduced coenzyme $Q_{10}$ crystal which comprises a crystallization of reduced coenzyme $Q_{10}$ in a solution of alcohols and/or ketones, reduced coenzyme $Q_{10}$ crystal excellent in slurry properties and crystalline properties maybe obtained. Moreover, an isolation process including a crystal separation or the whole process including the isolation process maybe minimized and simplified. Thus, highly pure reduced coenzyme $Q_{10}$ may be obtained in a high yield.

15 Claims, No Drawings

METHOD OF PRODUCING REDUCED COENZYME $Q_{10}$ CRYSTALS WITH EXCELLENT HANDLING PROPERTIES

TECHNICAL FIELD

The present invention relates to a method of producing a reduced coenzyme $Q_{10}$ crystal. Reduced coenzyme $Q_{10}$ shows a higher level of oral absorbability as compared with oxidized coenzyme $Q_{10}$ and is a compound useful as an ingredient in good foods, functional nutritive foods, specific health foods, nutritional supplements, nutrients, drinks, feeds, animal drugs, cosmetics, medicines, remedies, preventive drugs, etc.

BACKGROUND ART

Oxidized coenzyme $Q_{10}$, which is a benzoquinone derivative widely distributed in the biological world, is also called vitamin Q because of its vitamin-like function and is an ingredient acting as a nutrient in restoring the cell activity that has been weakened to its healthy condition and rejuvenating the body. On the other hand, reduced coenzyme $Q_{10}$, which is derived from oxidized coenzyme $Q_{10}$ by two-electron reduction, is as white crystals as compared with oxidized coenzyme $Q_{10}$ being as orange-colored crystals. Reduced coenzyme $Q_{10}$ and oxidized coenzyme $Q_{10}$ are known to be localized in the mitochondrion, lysosome, Golgi body, microsome, peroxisome, and cell membrane, among others, and involved, as constituents of the electron transport system, in ATP production and activation, in vivo antioxidant activity, and membrane stabilization; they are thus substances indispensable for body function maintenance.

It is known that reduced coenzyme $Q_{10}$ can be prepared by producing coenzyme $Q_{10}$ in the conventional manner, for example by synthesis, fermentation, or extraction from natural products, and concentrating a reduced coenzyme $Q_{10}$-containing eluate fraction resulting from chromatography (JP-Hei-10-109933-A). On that occasion, as described in the above-cited publication, the chromatographic concentration may be carried out after reduction of oxidized coenzyme $Q_{10}$ contained in the reduced coenzyme $Q_{10}$ with a reducing agent such as sodium borohydride or sodium dithionite (sodium hyposulfite), or reduced coenzyme $Q_{10}$ may be prepared by reacting the reducing agent mentioned above with an existing highly pure grade of coenzyme $Q_{10}$ (oxidized form).

However, the thus-obtained reduced coenzyme $Q_{10}$ cannot always be favorably crystallized without trouble but tends to occur as a low-purity crystalline, semisolid, or oily product containing such impurities as oxidized coenzyme $Q_{10}$. Moreover, even when crystallization could be achieved somehow, some troubles are occurred due to its poor slurry properties, etc. For example, poor slurry fluidity causes stirring trouble or difficulty in brushing away from a crystallization container, and poor filterability requires long period of time for crystal separation. Furthermore, solubility of reduced coenzyme $Q_{10}$ in various organic solvents tends to be high and there is such a problem that the crystallization yield is not always high.

In addition, reduced coenzyme $Q_{10}$ has a characteristic of being readily oxidized into oxidized coenzyme $Q_{10}$ by molecular oxygen. On a commercial production scale, complete oxygen elimination is very difficult to achieve and, furthermore, fairly long periods of time are required for individual operations, unlike laboratory scale production, so that residual oxygen exerts a great adverse effect. Prolonged time of an isolation process increases the risk of the above-mentioned oxidation, and is directly connected with such yield and quality problems as the formation of hardly eliminable oxidized coenzyme $Q_{10}$ and immixture of the oxidized coenzyme $Q_{10}$ into the product.

Under such circumstances, it has been strongly desired to establish a crystallization method for improving slurry properties and crystalline properties thereby producing reduced coenzyme $Q_{10}$ with sufficient filterability in a high yield, and to establish a production method in which an isolation process including a crystal separation or the whole process including said isolation process, for producing highly pure reduced coenzyme $Q_{10}$, are shortened and simplified.

SUMMARY OF THE INVENTION

In view of the foregoing, the present invention has another object to provide an outstanding production method for obtaining reduced coenzyme $Q_{10}$ in the form of crystals which is suited for the production thereof on a commercial scale.

As a result of intensive investigations to cause good crystal growth of a reduced coenzyme $Q_{10}$ crystal, the present inventors found that a reduced coenzyme $Q_{10}$ crystal having excellent slurry properties and crystalline properties may be obtained in a high yield by crystallizing reduced coenzyme $Q_{10}$ from an solution of an alcohol and/or a ketone, thereby completed the present invention.

Thus, the present invention relates to a method of producing reduced coenzyme $Q_{10}$ crystals which comprises crystallizing reduced coenzyme $Q_{10}$ in a solution of an alcohol and/or a ketone.

Furthermore, the present invention relates to the above-mentioned method wherein reduced coenzyme $Q_{10}$ is crystallized from a solution an alcohol and/or a ketone containing reduced coenzyme $Q_{10}$ obtainable by reducing oxidized coenzyme $Q_{10}$ into reduced coenzyme $Q_{10}$ in a solution of an alcohol and/or ketone.

According to the method of the present invention, it becomes possible to shorten and simplify the isolation process including a crystal separation or the whole process including said isolation process, and thus, highly pure reduced coenzyme $Q_{10}$ can be obtained in a high yield.

DETAILED DESCRIPTION OF THE INVENTION

Hereafter, the present invention is described in detail.

First of all, the method of producing a reduced coenzyme $Q_{10}$ crystal, i.e., the method of crystallizing reduced coenzyme $Q_{10}$ is explained.

The method for producing a reduced coenzyme $Q_{10}$ crystal of the present invention is to crystallize reduced coenzyme $Q_{10}$ from an alcohol and/or ketone solution. Preferably, an alcohol is used.

Reduced coenzyme $Q_{10}$ used for crystallization may be obtained by conventional methods such as synthesis, fermentation or extraction from a natural product. Preferably, it is obtained by reducing oxidized coenzyme $Q_{10}$ contained in reduced coenzyme $Q_{10}$, or by reducing oxidized coenzyme $Q_{10}$, and more preferably it is obtained by using the reduction reaction of the present invention described below.

Although the crystallization method of the present invention is applicable to a source containing oxidized coenzyme $Q_{10}$ at a relatively high ratio, it is especially effective for highly pure reduced coenzyme $Q_{10}$ prepared by the reduction method mentioned below, etc. In the practice of the invention, it is very effective to purify and crystallize reduced coenzyme $Q_{10}$ with simultaneous removal of impurities contained in the reaction mixture or extract obtained in the conventional manner or produced by the above-mentioned reduction method or the like. On that occasion, the impurities should preferably be eliminated into the mother liquor. This makes it possible to remove coexisting impurities, in particular analogous compounds having a similar structure and generally not always easy to remove (specifically, reduced coenzyme $Q_9$, reduced coenzyme $Q_8$, reduced coenzyme $Q_7$, etc.). Alcohols and/or ketones are particularly effective solvents for removing the compounds having similar structures as mentioned above. Needless to say, it is very effective to utilize the method as a method of recrystallizing reduced coenzyme $Q_{10}$ crystals.

The most preferable mode of the present invention is a direct isolation method (one-pot method) which comprises crystallizing (preferably purifying and crystallizing) reduced coenzyme $Q_{10}$ from a solution obtained by reducing oxidized coenzyme $Q_{10}$ into reduced coenzyme $Q_{10}$ in a solution of an alcohol and/or a ketone (preferably an alcohol). Herewith, high-quality crystals having good properties may be obtained at a high yield in a quite simple and efficient manner.

The alcohols may be used for the present invention are not particularly restricted but may be cyclic or acyclic, or saturated or unsaturated. Saturated ones are preferred, however. For example, as a monohydric alcohol, there may be mentioned one containing 1 to 20 carbon atoms, preferably 1 to 12 carbon atoms, more preferably 1 to 6 carbon atoms, still more preferably 1 to 5 carbon atoms, and most preferably 1 to 3 carbon atoms. Most preferred is a monohydric alcohol containing 2 or 3 carbon atoms. Moreover, a dihydric alcohol containing 2 to 5 carbon atoms, preferably containing 2 to 3 carbon atoms, and a trihydric alcohol containing 3 carbon atoms, etc. may be also preferably used. Among the above, a monohydric alcohol containing 1 to 5 carbon atoms have high miscibility with water, and is preferably used when used as a mixed solvent with water.

As the monohydric alcohol, there may be mentioned, for example, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-l-pentanol, 4-methyl-2-pentanol, 2-ethyl-l-butanol, 1-heptanol, 2-heptanol, 3-heptanol, 1-octanol, 2-octanol, 2-ethyl-l-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, etc.

Preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-l-butanol and cyclohexanol. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol and neopentyl alcohol. Still more preferred are methanol, ethanol, 1-propanol, 2-propanol, 1-butanol, 2-butanol, isobutyl alcohol, 2-methyl-1-butanol and isopentyl alcohol. Further preferred are methanol, ethanol, 1-propanol and 2-propanol, particularly preferred are ethanol, 1-propanol and 2-propanol, and most preferred is ethanol.

As the dihydric alcohol, there may be mentioned, for example, 1,2-ethanediol, 1,2-propandiol, 1,3-propandiol, 1,2-butanediol, 1,3-butanediol, 1,4-butanediol, 2,3-butanediol, 1,5-pentanediol, etc. Preferred are 1,2-ethanediol, 1,2-propandiol and 1,3-propandiol, and most preferred is 1,2-ethanediol.

As the trihydric alcohol, glycerol, etc. may be preferably used, for example.

The ketones are not particularly restricted, and ones having 3 to 6 carbon atoms are preferably used. As specific examples, there may be mentioned, for example, acetone, methyl ethyl ketone, methyl butyl ketone, methyl isobutyl ketone, etc. Preferred are acetone and methyl ethyl ketone, and most preferred is acetone.

The method of crystallization is not particularly restricted and the crystallization is carried out by utilizing at least one of the cooling crystallization, concentration crystallization, solvent substitution crystallization and other methods. The solubility of reduced coenzyme $Q_{10}$ in alcohols and/or ketones shows very preferable temperature dependency, which suitably contributes to favorably reduce the amount of reduced coenzyme $Q_{10}$ in solution and convert the same into a crystalline state in a high yield. For exhibiting this characteristic to the utmost extent, it is particularly preferred to utilize the cooling crystallization method, or a combination of the cooling crystallization method with some other method of crystallization.

The crystallization concentration is an important factor and, as the concentration at the time of completion of crystallization, when expressed in terms of the weight of reduced coenzyme $O_{10}$ based on the weight of the crystallization solvent at the time of completion of crystallization, it is preferably not higher than about 15 w/w %, more preferably not higher than about 13 w/w %, still more preferably not higher than 10 w/w %. By maintaining such a concentration as mentioned above, it becomes possible to favorably carry out the crystallization in a manner adapted to the handling properties on an industrial scale. From the productivity viewpoint, the lower limit to the crystallization concentration is generally not lower than about 1 w/w %, preferably not lower than about 2 w/w %.

The above-mentioned crystallization is preferably carried out under forced flowing. For preventing the state of supersaturation from occurring and thereby allowing the nucleation and crystal growth to proceed smoothly and, furthermore, from the viewpoint of obtaining high-quality products, the flowing is generally brought about by a stirring power per unit volume of not weaker than about 0.01 kW/m³, preferably not weaker than about 0.1 kW/m³, and more preferably not weaker than about 0.3 kW/m³. The forced flowing is generally provided by the turning of a stirring blade(s). However, the use of a stirring blade(s) is not always necessary if the above flowing can be otherwise obtained. For example, it is possible to utilize a method based on liquid circulation.

In carrying out the crystallization, seed crystals are preferably added so that the state of supersaturation may be prevented from occurring and the nucleation and crystal growth may be allowed to proceed smoothly.

The crystallization temperature (the cooling temperature in the step of crystallization) is not particularly restricted, but from the yield viewpoint, it is preferably not higher than 25° C., more preferably not higher than 20° C., still more preferably not higher than 15° C., and particularly preferably not higher than 10° C. The lower limit is the solidification temperature of the system. Thus, the crystallization can be advantageously carried out generally at a cooling temperature of preferably about 0° C. to 25° C.

In the process of crystallization, it is preferable to control the formation of supersaturation by controlling the amount of crystals crystallizing out per unit time. A preferred rate of crystallization per unit time is, for example, not higher than the rate of crystallization which causes crystallization of about 50%, per unit time, of the whole amount of crystals to be obtained (i.e. at most 50%/hour), preferably not higher than the rate of crystallization which causes crystallization of about 25%, per unit time, of the whole amount of crystals to be obtained (i.e. at most 25%/hour). The rate of cooling in the crystallization by cooling is generally not higher than about 40° C./hour, and preferably not higher than about 20° C./hour.

In the crystallization method of the present invention, generally, it is preferable to use the above-mentioned solvents in view of the slurry properties and crystalline properties obtainable by crystallization, but other solvents except for the above alcohols and/or ketones may coexist or may be added.

The other solvents are not particularly restricted, but for example, hydrocarbons, fatty acid esters, ethers, fatty acids, nitrogen-containing compounds (including nitriles and amides), sulfur-containing compounds, water, etc. may be mentioned.

As the hydrocarbons, fatty acid esters, ethers and nitriles, the solvents mentioned below may be preferably used as a solvent for the reduction reaction.

As the fatty acids, there may be mentioned, for example, formic acid, acetic acid, propionic acid, etc. Preferred are formic acid and acetic acid, and most preferred is acetic acid.

As nitrogen-containing compounds other than nitriles, there maybe mentioned, for example, nitromethane, triethylamine, pyridine, formamide, N-methylformamide, N,N-dimethylformamide, N,N-dimethylacetoamide, N-methylpyrrolidone, etc.

As the sulfur-containing compounds, for example, dimethyl sulfoxide, sulfolane, etc. may be mentioned.

It is effective to use these other solvents with the alcohol and/or ketone solution mentioned above at a preferable ratio according to characteristics of these solvents in order to improve conditions determining crystallization conditions such as solubility, crystallization concentration, yield, slurry properties and crystalline properties of reduced coenzyme $Q_{10}$.

Among the other solvents mentioned above, water is particularly preferably used in view of obtaining high yield by suitably decreasing the solubility of reduced coenzyme $Q_{10}$, improving the slurry properties, and what is particularly to be noted, significantly improving solid-liquid dissolubility (filterability).

The ratio of these other solvents and the above-mentioned alcohols and/or ketones depends on the solvent species and thus cannot be absolutely specified, and is not particularly restricted provided that it is a solvent comprising the above-mentioned alcohols and/or ketones substantially as a main component. Preferably, the ratio of the above alcohols and/or ketones in the solvent is about 80 w/w % or more as the sum total of alcohols and ketones, more preferably about 90 w/w % or more, still more preferably about 93 w/w % or more.

In particular, when water is used as an auxiliary solvent in view of the improvement of the solid liquid dissolubility mentioned above, the lower limit of the ratio of the above alcohols and/or ketones in a solvent is about 90 w/w % or more, preferably about 91 w/w % or more, more preferably about 92 w/w % or more, and still more preferably about 93 w/w % or more. The upper limit is about 99.5 w/w % or less, preferably about 99 w/w % or less, more preferably about 98 w/w % or less, and still more preferably about 97 w/w % or less. Generally, the range between about 90 w/w % and about 99.5 w/w % is preferable, and the range between about 93 w/w % and about 97 w/w % is most preferable.

Preferably, the thus-obtained crystals of reduced coenzyme $Q_{10}$ can be recovered as a wet product, for example, by such a solid-liquid separation technique as centrifugation, pressure filtration, or vacuum filtration, if necessary followed by cake washing using the solvents described in the present inventions including the above-mentioned alcohols or ketones. They can be recovered also as a dry product by further charging the wet product in a reduced pressure drier (vacuum drier) internally purged with an inert gas and drying the same under reduced pressure. The recovery in a dry form is preferred.

It is effective to carry out the production method of the present invention in a deoxygenated atmosphere in view of protection from oxidation. The deoxygenated atmosphere can be attained by substitution with an inert gas, pressure reduction, boiling, or a combination of these. It is preferable to carry out at least the substitution with an inert gas, namely to use an inert gas atmosphere. As the inert gas, there maybe mentioned, for example, nitrogen gas, helium gas, argon gas, hydrogen gas, and carbon dioxide gas. Nitrogen gas is preferred, however.

Next, a method for synthesizing reduced coenzyme $Q_{10}$ suitably used in the present invention, i.e., a reaction for reducing oxidized coenzyme $Q_{10}$ into reduced coenzyme $Q_{10}$ is described.

As mentioned above, the above reduction reaction is preferably carried out in the solution of an alcohol and/or a ketone described in the above crystallization method and subjected to the direct isolation method (one-pot method). Thereby, the operations may be simplified and shortened to minimize oxidation by molecular oxygen. In this case, ascorbic acid and a related compound thereof mentioned below are the particularly preferable reducing agents.

Moreover, it is also preferable to use a solvent having high protection effect from oxidation to carry out the above-mentioned reduction reaction and/or extraction and water-washing operation(s) in order to protect reduced coenzyme $Q_{10}$ from oxidation by molecular oxygen even when the operation time is prolonged.

As such solvent having high protection effect from oxidation, it is preferable to use at least one species selected from hydrocarbons, fatty acid esters, ethers and nitriles, and most preferably hydrocarbons.

The hydrocarbons are not particularly restricted, but there may be mentioned, for example, aliphatic hydrocarbons, aromatic hydrocarbons, halogenated hydrocarbons, etc. Preferred are aliphatic hydrocarbons and aromatic hydrocarbons, and more preferred are aliphatic hydrocarbons.

The aliphatic hydrocarbons are not particularly restricted, and may be cyclic or acyclic, or saturated or unsaturated. However, generally they contain 3 to 20 carbon atoms, and preferably 5 to 12 carbon atoms.

As specific examples, there may be mentioned, for example, propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, etc.

Among them, saturated aliphatic hydrocarbons having 5 to 8 carbon atoms are more preferred, and preferably used are pentane, 2-methylbutane and cyclopentane, which have 5 carbon atoms (referred to as "pentanes"); hexane, 2-methylpentane, 2,2-dimethylbutane, 2,3-dimethylbutane, methylcyclopentane, cyclohexane, which have 6 carbon atoms (referred to as "hexanes"); heptane, 2-methylhexane, 3-methylhexane, 2,3-dimethylpentane, 2,4-dimethylpentane, methylcyclohexane, which have 7 carbon atoms (referred to as "heptanes"); octane, 2,2,3-trimethylpentane, isooctane, ethylcyclohexane, which have 8 carbon atoms (referred to as octanes); and a mixture of these. In particular, the above heptanes are particularly preferred since they have a tendency to show a very high protection effect against oxidization, and heptane is most preferred.

The aromatic hydrocarbons are not particularly restricted, but generally they contain 6 to 20 carbon atoms, preferably 6 to 12 carbon atoms, and more preferably 7 to 10 carbon atoms. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, etc. Preferred are toluene, xylene, o-xylene, m-xylene, p-xylene, ethylbenzene, cumene, mesitylene, tetralin, butylbenzene, p-cymene, cyclohexylbenzene, diethylbenzene and pentylbenzene. More preferred are toluene, xylene, o-xylene, m-xylene, p-xylene, cumene and tetralin, and most preferred is cumene.

The halogenated hydrocarbons are not particularly restricted, and may be cyclic or acyclic, or saturated or unsaturated. However, acyclic halogenated hydrocarbons are preferably used. More preferred are chlorinated hydrocarbons and fluorinated hydrocarbons, and chlorinated hydrocarbons are still more preferred. Additionally, ones containing 1 to 6 carbon atoms, preferably 1 to 4 carbon atoms, and more preferably 1 to 2 carbon atoms are used.

As specific examples, for example, there may be mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, etc.

Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene and 1,1,1,2-tetrafluoroethane. More preferred are dichloromethane, chloroform, 1,2-dichloroethylene, trichloroethylene, chlorobenzene and 1,1,1,2-tetrafluoroethane The fatty acid esters are not particularly restricted, but there may be mentioned, for example, propionates, acetates, formates, etc. Preferred are acetates and formates, and more preferred are acetates. Ester functional groups thereof are not particularly restricted, but alkyl esters having 1 to 8 carbon atoms, aralkyl esters having 1 to 8 carbon atoms, preferred are alkyl esters having 1 to 6 carbon atoms, and more preferred are alkyl esters having 1 to 4 carbon atoms are used.

As the propionates, there may be mentioned, for example, methyl propionate, ethyl propionate, butyl propionate, isopentyl propionate, etc. Preferred is ethyl propionate.

As the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, etc. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate and cyclohexyl acetate. More preferred are methyl acetate, ethyl acetate, propyl acetate, isopropyl acetate, butyl acetate and isobutyl acetate. Most preferred is ethyl acetate.

As the formates, there may be mentioned, for example, methyl formate, ethyl formate, propyl formate, isopropyl formate, butyl formate, isobutyl formate, sec-butyl formate, pentyl formate, etc. Preferred are methyl formate, ethyl formate, propyl formate, butyl formate, isobutyl formate and pentyl formate, and most preferred is ethyl formate.

The ethers are not particularly restricted, and may be cyclic or acyclic, or saturated or unsaturated. But saturated ones are preferably used. Generally, ones containing 3 to 20 carbon atoms, and preferably 4 to 12 carbon atoms and more preferably 4 to 8 carbon atoms are used. As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether, etc.

Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether. More preferred are diethyl ether, methyl tert-butyl ether, anisol, dioxane, tetrahydrofuran, ethylene glycol monomethyl ether and ethylene glycol monoethyl ether. More preferred are diethyl ether, methyl tert-butyl ether, anisol, etc., and most preferred is methyl tert-butyl ether.

The nitriles are not particularly restricted, and may be cyclic or acyclic, or saturated or unsaturated. However, saturated ones are preferably used. Generally, ones containing 2 to 20 carbon atoms, preferably 2 to 12 carbon atoms, and more preferably 2 to 8 carbon atoms are used.

As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, etc.

Preferred are acetonitrile, propiononitrile, butyronitrile, isobutyronitrile, succinonitrile, valeronitrile, chloropropiononitrile, methyl cyanoacetate, ethyl cyanoacetate, tolunitrile and benzonitrile. More preferred are acetonitrile, propiononitrile, butyronitrile and isobutyronitrile, and most preferred is acetonitrile.

In selecting the solvent to be used from among the solvents mentioned above, such properties as boiling point and viscosity are preferably taken into consideration; for example, the solvent should have a boiling point which allows appropriate warming for increasing the solubility and facilitates a solvent removal from wet masses by drying and solvent recovery from crystallization filtrates (about 30 to 150° C. at 1 atmosphere), a melting point such that solidification hardly occurs in handling at room temperature as well as upon cooling to room temperature or below (not higher than about 20° C., preferably not higher than about 10° C., still more preferably not higher than about 0° C.), and a low viscosity (not higher than about 10 cp at 20° C.). From the industrial operation viewpoint, a solvent which is scarcely volatile at ordinary temperature is preferred; for example, one having a boiling point of not lower than about 80° C. is preferred, and one having a boiling point of not lower than about 90° C. is more preferred.

Reduced coenzyme $Q_{10}$, when in a dissolved state, tends to become more resistant to oxidation as the concentration thereof increases. Reduced coenzyme $Q_{10}$ is highly soluble in the solvents mentioned above and, in this respect, too, the above solvents are suitable for the protection from oxidation. The concentration of reduced coenzyme $Q_{10}$ which is preferred from the viewpoint of protection thereof from oxidation may vary depending on the solvent species, among others, hence cannot be absolutely specified. Generally, however, the concentration of reduced coenzyme $Q_{10}$ in the above solvents is generally not lower than 1 w/w %, and preferably not lower than 2 w/w %. The upper limit is not particularly restricted but, from the practical operability viewpoint, it is 400 w/w % or below, preferably 200 w/w % or below, more preferably 100 w/w % or below, and still more preferably 50 w/w % or below.

Accordingly, unfavorable side reactions by oxygen may be minimized by the use of the above-mentioned solvent through the whole process of the reduction reaction.

The reduction reaction may be carried out using, as the reducing agent, a metal hydride compound, iron (metallic iron or iron in a salt form), zinc (metallic zinc), hyposulfurous acid or a salt thereof, or ascorbic acid or a related compound thereof, for instance.

Moreover, the reduction using a metal hydride compound, iron (metallic iron or iron in a salt form), zinc (metallic zinc), or hyposulfurous acid or a salt thereof is preferably carried out in the above-mentioned solvent with high oxidation-protective effect. Furthermore, the reduction using ascorbic acid or a related compound thereof may be carried out using various solvents such as alcohols and/or ketones, as well as the above-mentioned solvent having high protection effect from oxidation, but preferably carried out using an alcohol (especially preferred is an alcohol having high miscibility with water), an ether having high miscibility with water, a nitrile having high miscibility with water, and a ketone having high miscibility with water.

The metal hydride compound is not particularly restricted but includes, among others, sodium borohydride and lithium aluminum hydride. The amount to be used of the metal hydride compound may vary depending on the species thereof, hence cannot be absolutely specified. Generally, however, the reduction can be favorably carried out by using it in an amount of 1 to 3 times theoretical hydrogen equivalent.

The reduction using iron or zinc is generally carried out using an acid. The acid is not particularly restricted but includes, among others, fatty acids such as acetic acid, sulfonic acids such as methanesulfonic acid, and inorganic acids such as hydrochloric acid and sulfuric acid. Inorganic acids are preferred, and sulfuric acid is more preferred.

The amount of iron to be used is not particularly restricted but, for example, an amount of about ⅕ by weight or larger based on the charged weight of oxidized coenzyme $Q_{10}$ is appropriate for carrying out the reaction. The upper limit is not particularly restricted but, from the economical viewpoint, it is about twice the weight of the above charged weight or lower. Iron may be used not only in the form of metallic iron but also in the form of a salt, for example iron (II) sulfate, etc.

The amount of zinc to be used is not particularly restricted but, for example, an amount of about ¹⁄₁₀ by weight or larger based on the charged weight of oxidized coenzyme $Q_{10}$ is appropriate for carrying out the reaction. The upper limit is not particularly restricted but, from the economical viewpoint, it is about twice the weight of the above charged weight or lower.

The hyposulfurous acid or a salt thereof is not particularly restricted but a salt form of hyposulfurous acid is generally used. The salt of hyposulfurous acid is not particularly restricted but includes, as preferred species, alkali metal salts, alkaline earth metal salts, ammonium salt and the like. Alkali metal salts such as the lithium salt, sodium salt, and potassium salt are more preferred, and the sodium salt is most preferred. The amount to be used of the hyposulfurous acid or salt is not particularly restricted but it is generally not smaller than about ⅕ by weight, preferably not smaller than about ⅖ by weight, and more preferably not smaller than about ⅗ by weight, based on the charged weight of oxidized coenzyme $Q_{10}$. Larger amounts may be used without causing any particular trouble. From the economical viewpoint, however, the amount to be employed is not larger than about twice the weight of the above-mentioned charged weight, preferably not larger than the charged weight. Thus, the reaction can be more favorably carried out with employing an amount within the range of about ⅖ by weight of the above-mentioned charge to a weight roughly equal to that of the charged weight.

The ascorbic acid or a related compound thereof are not particularly restricted, and include, for example, not only ascorbic acid, but also rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, and the like related compounds, and may be ester forms or salts of these. Furthermore, these may be L-form, D-form or racemic form. More specifically, there may be mentioned, for example, L-ascorbic acid, L-ascorbyl palmitate, L-ascorbyl stearate, D-arabo-ascorbic acid, etc. In producing the reduced coenzyme $Q_{10}$, any of the above-mentioned ascorbic acid and related compounds thereof maybe suitably used. However, the water-soluble ones are suitably used in particular among the above-mentioned ascorbic acid or related compounds thereof in view of separatability with the generated reduced coenzyme $Q_{10}$, etc. And most preferred is a free form of L-ascorbic acid, D-arabo-ascorbic acid and the like in view of the ready availability, price, etc.

The amount to be used of the ascorbic acid or a related compound thereof mentioned above is not particularly restricted but may be an amount effective in converting oxidized coenzyme $Q_{10}$ into reduced coenzyme $Q_{10}$. Generally it is not smaller than 1 mole, preferably not smaller than 1.2 moles, per mole of oxidized coenzyme $Q_{10}$. The upper limit is not particularly restricted but, from the economical viewpoint, it is generally not higher than 10 moles, preferably not higher than 5 moles, and more preferably not higher than 3 moles, per mole of the oxidized coenzyme $Q_{10}$.

Among the reducing agent species mentioned above, zinc, hyposulfurous acid and salts thereof, and ascorbic acid and related compounds thereof are preferred from the viewpoint of reducing ability, yield and/or quality, among others, and, in particular, hyposulfurous acid (specifically hyposulfurous acid salts) and ascorbic acid or related compounds thereof are preferred.

In carrying out the reduction reaction, water and/or an alcohol are/is suitably used singly or in combination. Water is preferred in particular when iron, zinc, or hyposulfurous acid or a salt thereof is used as the reducing agent. When a metal hydride compound is used as the reducing agent, an alcohol can be used in combination. The combined use of water and an alcohol exhibits the characteristics of both water and the alcohol, and contributes to improvements in reaction rate and yield, among others.

In the following, a preferred method of reduction is described in detail.

The reduction using hyposulfurous acid or a salt thereof is preferably carried out using water in combination, namely in a mixed solvent system composed of at least one organic solvent selected from among the above-mentioned hydrocarbons, fatty acid esters, ethers, and nitriles (preferably hydrocarbons, more preferably aliphatic hydrocarbons, still more preferably heptanes, and particularly preferably heptane), with water. On that occasion, the reaction is preferably carried out generally at pH of not higher than 7, preferably at pH 3 to 7, more preferably at pH 3 to 6, from the viewpoint of yield, etc. The pH can be adjusted using an acid (e.g. an inorganic acid such as hydrochloric acid or sulfuric acid) or a base (e.g. an alkali metal hydroxide such as sodium hydroxide).

In the reduction using hyposulfurous acid or a salt thereof, the amount of water is not particularly restricted but may be an amount of water such that an appropriate amount of the reducing agent, namely hyposulfurous acid or a salt thereof, can be dissolved therein. Thus, for example, it is advisable that the amount of the hyposulfurous acid or a salt be adjusted generally to not more than 30 w/w %, and preferably not more than 20 w/w %, relative to the weight of water. From the productivity viewpoint, among others, it is advisable that the amount be adjusted generally to not less than 1 w/w %, preferably not less than 5 w/w %, and more preferably not less than 10 w/w %.

The reduction using the ascorbic acid or a related compound thereof mentioned above may be preferably carried out using a solvent especially highly miscible with water as selected from among the above-mentioned hydrocarbons, fatty acid esters, ethers, and nitriles, in particular ethers and nitriles, which are highly miscible with water, and more specifically tetrahydrofuran, dioxane, acetonitrile or the like. But it is particularly preferable to use the alcohol and/or ketone mentioned above used in crystallization method of the present invention (preferably an alcohol and/or ketone having high miscibility with water (specifically, as an alcohol, amonohydric or a dihydric (preferably monohydric) alcohol containing 1 to 5 carbon atoms, preferably containing 1 to 4 carbon atoms, and more preferably containing 1 to 3 carbon atoms, and as a ketone, acetone, methyl ethyl ketone, etc.)).

In the reduction using the ascorbic acid or a related compound thereof, from the viewpoint of reaction promotion (e.g. reaction temperature lowering or reaction time shortening), it is possible to carry out the reduction in the presence of an additive having a reaction promoting effect, such as a basic substance or a hydrogensulfite salt.

The basic substance is not particularly restricted but may be either an inorganic compound or an organic compound. The inorganic compound is not particularly restricted but includes, among others, the hydroxides, carbonates, and hydrogencarbonates of metals (preferably alkali metals, alkaline earth metals, and the like), and ammonia. As typical examples thereof, there may be mentioned alkali metal hydroxides such as sodium hydroxide, alkali metal carbonates such as sodium carbonate, alkali metal hydrogencarbonates such as sodium hydrogencarbonate, and alkaline earth metal carbonates such as magnesium carbonate. The organic compound is not particularly restricted but includes, among others, amines such as triethylamine. Among the basic substances specifically mentioned above, weakly basic substances (weak bases or weak alkalis) such as the carbonates and hydrogencarbonates of metals (preferably alkali metals, alkaline earth metals, etc.), ammonia, and like inorganic compounds; amines such as triethylamine, and like organic compounds are preferably used. More preferred are the weakly basic inorganic compounds mentioned above.

Preferred as the hydrogensulfite are, for example, alkali metal hydrogensulfites such as sodium hydrogensulfite.

The amount of the additive mentioned above is not particularly restricted but may be such that the reaction promoting effect of the additive can be produced to a desired extent (effective amount). From the economical viewpoint, however, the amount is generally not more than 20 moles, preferably not more than 10 moles, more preferably not more than 5 moles, and still more preferably not more than 2 moles, per mole of the ascorbic acid or a related compound thereof. The lower limit is not particularly restricted but, generally, it is not less than 0.01 moles, preferably not less than 0.05 moles, more preferably not less than 0.1 moles, and still more preferably not less than 0.2 moles, per mole of the ascorbic acid or a related compound thereof.

The reduction reaction described in the present invention is preferably carried out under forced flowing. The power required for stirring to cause such flowing per unit volume is generally not less than about 0.01 kW/m$^3$, preferably not less than about 0.1 kW/m$^3$, and more preferably not less than about 0.3 kW/m$^3$. The above forced flowing is generally caused by the turning of a stirring blade(s). The use of a stirring blade(s) is not always necessary if the above flowing can be otherwise obtained. For example, a method based on liquid circulation may be utilized.

The reduction temperature may vary depending on the reducing agent species and/or amount, hence cannot be absolutely specified. In the reduction using hyposulfurous acid or a salt thereof, for instance, the reduction is generally carried out at 100° C. or below, preferably at 80° C. or below, more preferably at 60° C. or below. The lower limit is the solidification temperature of the system. Thus, the reduction can be favorably carried out generally at about 0 to 100° C., preferably at about 0 to 80° C., more preferably at about 0 to 60° C. In the reduction using ascorbic acid or a related compound thereof, the reduction is carried out generally at 30° C. or higher, preferably at 40° C. or higher, more preferably at 50° C. or higher. The upper limit is the boiling point of the system. Thus, the reduction can be favorably carried out generally at about 30 to 150° C., preferably about 40 to 120° C., and more preferably at about 50 to 100° C.

The reaction concentration is not particularly restricted but the weight of oxidized coenzyme $Q_{10}$ relative to the solvent weight is generally not less than about 1 w/w %, preferably not less than 3 w/w %, more preferably not less than 10 w/w %, and still more preferably not less than 15 w/w %. The upper limit is not particularly restricted but generally is not higher than about 60 w/w %, preferably not higher than 50 w/w %, more preferably not higher than 40 w/w %, and still more preferably not higher than 30 w/w %. Thus, the reaction can be favorably carried out at a reaction concentration of about 1 to 60 w/w %, preferably about 3 to 50 w/w %, and more preferably about 10 to 40 w/w %. The reduction reaction time may vary depending on the reducing agent species and/or the amount thereof, hence cannot be absolutely specified. Generally, however, the reaction can be driven to completion within 48 hours, preferably within 24 hours, more preferably within 10 hours, and still more preferably within 5 hours.

It is exceedingly preferable to carry out the reduction reaction in a deoxygenated atmosphere. Surprisingly, it was found that, in the reduction reaction using hyposulfurous acid or a salt thereof, in particular, such atmosphere greatly contributes to an improvement in reduction reaction yield and a reduction in reducing agent amount. The deoxygenated atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, and carbon dioxide gas. Nitrogen gas is preferred, however.

An organic phase containing the product reduced coenzyme $Q_{10}$ is recovered from the thus-obtained reduction reaction mixture and, if necessary (preferably), the organic phase is further washed repeatedly using water, brine or the like to achieve complete contaminant elimination, followed by carrying out solvent substitution with an alcohol and/or a ketone to give a solution for the above-mentioned crystallization.

In view of the protection from oxidation, it is preferable to carrying out solvent substitution of the solution prepared by dissolving reduced coenzyme $Q_{10}$ in at least one species of solvents selected from hydrocarbons, fatty acid esters, ethers and nitriles with an alcohol and/or a ketone.

Particularly, when the hyposulfurous acid or a salt thereof mentioned above, such as sodium hyposulfite, is used as the reducing agent, it is desirable to repeat washing with water so that contaminants derived from the hyposulfurous acid or salt thereof may be removed completely and/or the pH of the aqueous phase may be stabilized.

Moreover, as described above, when the reduction is carried out with ascorbic acid or a related compound thereof using the alcohol and/or ketone used in the crystallization method of the present invention (preferably, an alcohol and/or a ketone having high miscibility with water (specifically, as an alcohol, a monohydric or dihydric alcohol (preferably monohydric) containing 1 to 5 carbon atoms, preferably 1 to 4 carbon atoms, and more preferably 1 to 3 carbon atoms, and as ketones, acetone, methyl ethyl ketone, etc.), it is quite convenient and efficient to crystallize reduced coenzyme $Q_{10}$ directly from a reduction reaction solution (direct isolation method (one-pot method)) according to the above-mentioned crystallization method. In that case, it is preferable to crystallize reduced coenzyme $Q_{10}$ by cooling, concentrating, or poor solvent-addition (preferably water addition), more preferably by cooling or concentrating, and still more preferably by cooling, after carrying out the reduction reaction in the above-mentioned method. In addition, the solvent to be used in the reduction reaction is not particularly restricted in this case, but preferably a solvent comprising the above alcohol and/or ketone as a main component(s).

Generally, the ratio of the above-mentioned alcohol and/or ketone in the solvent is about 50 w/w % or more, preferably about 60 w/w % or more and more preferably about 70 w/w % or more in view of the reaction rate and reaction yield. But in considering the application to the following crystallization, it is still more preferably about 80 w/w % or more, particularly preferably about 90 w/w % or more and most preferably about 93 w/w % or more.

When water is combinedly used at the time of reaction, the lower limit of the ratio of the above-mentioned alcohols and/or ketones in the solvent is about 90 w/w % or more, preferably about 91 w/w % or more, more preferably about 92 w/w % or more, and still more preferably about 93 w/w % or more. The upper limit is about 99.5 w/w % or less, preferably about 99 w/w % or less, more preferably about 98 w/w % or less, and still more preferably about 97 w/w % or less. The range between 93 w/w % and 97 w/w % is most preferable.

In accordance with the present invention, a high-quality reduced coenzyme $Q_{10}$ crystal may be obtained with excellent workability and economical efficiency. The crystals of reduced coenzyme $Q_{10}$ as obtained in accordance with the present invention can be expected to have a reduced coenzyme $Q_{10}$/oxidized coenzyme $Q_{10}$ weight ratio of not lower than 96/4, preferably not lower than 98/2, more preferably not lower than 99/1.

BEST MODE FOR CARRYING OUT THE INVENTION

The following examples illustrate the present invention in further detail. These examples are, however, by no means limitative of the scope of the present invention. In the examples, the purity of reduced coenzyme $Q_{10}$ and the reduced coenzyme $Q_{10}$/oxidized coenzyme $Q_{10}$ weight ratio were determined by the HPLC analysis specified below. The reduced coenzyme $Q_{10}$ purity values as determined, however, are by no means indicative of the limit purity value attainable in accordance with the present invention. Likewise, the reduced coenzyme $Q_{10}$/oxidized coenzyme $Q_{10}$ weight ratio values obtained never indicate the upper limit to that ratio. (HPLC Conditions) Column: SYMMETRY C18 (product of Waters), 250 mm (in length), 4.6 mm (in inside diameter); mobile phase: $C_2H_5OH:CH_3OH=4:3$ (v/v); detection wavelength: 210 nm; flow rate: 1 ml/min; retention time of reduced coenzyme $Q_{10}$: 9.1 min; retention time of oxidized coenzyme $Q_{10}$: 13.3 min.

EXAMPLE 1

Oxidized coenzyme $Q_{10}$ (100 g; containing 0.40% of oxidized coenzyme $Q_9$, purity 99.4%) was dissolved in 1000 g of heptane at 25° C. While stirring (power required for stirring: 0.3 kW/m³), an aqueous solution prepared by dissolving 100 g of sodium hyposulfite (purity: at least 75%), as the reducing agent, in 1000 ml of water was gradually added and the reduction reaction was carried out at 25° C. and at pH 4 to 6. After the lapse of 2 hours, the aqueous phase was removed from the reaction mixture, and the heptane phase was washed 6 times with 1000 g of deaerated saturated brine. All the above operations were carried out in a nitrogen atmosphere. This heptane phase was subjected to solvent substitution under reduced pressure to prepare a 7% (w/w) ethanol solution of reduced coenzyme $Q_{10}$ at 50° C. was prepared (containing 100 g of reduced coenzyme $Q_{10}$ (containing 0.40% of reduced coenzyme $Q_9$)). Moreover, the solution was cooled to 2° C. at cooling rate of 10° C./hour while stirring in a nitrogen atmosphere (power required for stirring 0.3 kW/m³) to precipitate a crystal. The slurry showed good fluidity and was easily brushed away from a crystallization container. The obtained slurry was filtered under reduced pressure, and the wet crystals were washed in sequence with cold ethanol, cold water and cold ethanol (the cold solvents used for washing having a temperature of 2° C.). The wet crystals were further dried under reduced pressure (20-40° C., 1-30 mmHg) to give 95 g of white dry crystals (containing 0.19% of reduced coenzyme $Q_9$, percentage of elimination: 53%) (isolated product yield: 95 mole %). The reduced coenzyme $Q_{10}$/oxidized coenzyme $Q_{10}$ weight ratio of the crystals obtained was 99.3/0.7, and the purity of the reduced coenzyme $Q_{10}$ was 99.0%. The slurry was filtered using a 20 cm-diameter Nutsche funnel with a filter spread thereon and depressurized by an aspirator. The time required for filtration was 12 minutes.

EXAMPLE 2

A series of operations from the reduction reaction to washing with water was carried out under the same conditions as in Example 1 to obtain a heptane solution of reduced coenzyme $Q_{10}$ (containing 100 g of reduced coenzyme $Q_{10}$ (containing 0.40% of reduced coenzyme $Q_9$)). This heptane solution was subjected to solvent substitution under reduced pressure to prepare a 7% (w/w) 2-propanol solution of reduced coenzyme $Q_{10}$ at 50° C. This solution was cooled to 2° C. at cooling rate of 10° C./hour while stirring in a nitrogen atmosphere to precipitate a crystal. The slurry showed good fluidity and was easily brushed away from a crystallization container. The obtained slurry was filtered under reduced pressure (filterability was good same as in Example 1), and the wet crystals were washed in sequence with cold 2-propanol, cold water and cold 2-propanol (the cold solvents used for washing having a temperature of 2° C.). Furthermore, the wet crystal was dried under reduced pressure (20-40° C., 1-30 mmHg) to obtain 94 g of white dry crystals (containing 0.20% of reduced coenzyme $Q_9$, percentage of elimination: 50%) (isolated product yield: 94 mol %). The reduced coenzyme $Q_{10}$/oxidized coenzyme $Q_{10}$ weight ratio of the crystals obtained was 99.3/0.7, and the purity of the reduced coenzyme $Q_{10}$ was 99.0%.

EXAMPLE 3

Oxidized coenzyme $Q_{10}$ (100 g; containing 0.40% of oxidized coenzyme $Q_9$, purity 99.4%) was dissolved in 1000 g of hexane at 25° C. While stirring (power required for stirring 0.3 kW/m$^3$), an aqueous solution prepared by dissolving 100 g of sodium hyposulfite (purity: at least 75%) in 1000 ml of water was gradually added as a reducing agent to carry out the reduction reaction at 25° C. and at pH of 4 to 6. After the lapse of 2 hours, an aqueous phase was removed from a reaction solution, and further a hexane phase was washed for 6 times with 1000 g of deaerated saturated brine. This hexane phase was subjected to solvent substitution under reduced pressure to prepare a 7% (w/w) acetone solution of reduced coenzyme $Q_{10}$ at 50° C. (containing 100 g of reduced coenzyme $Q_{10}$ (containing 0.40% of reduced coenzyme $Q_9$)). This solution was cooled to 2° C. at cooling rate of 10° C./hour while stirring in a nitrogen atmosphere (power required for stirring 0.3 kW/m$^3$) to precipitate a crystal. The slurry showed good fluidity and was easily brushed away from a crystallization container. The obtained slurry was filtered under reduced pressure (filterability was good same as in Example 1). The wet crystals were washed in sequence with cold acetone, cold water and cold acetone (the cold solvents used for washing having a temperature of 2° C.). Furthermore, the wet crystal was dried under reduced pressure (20-40° C., 1-30 mmHg) to obtain 93 g of white dry crystals (containing 0.21% of reduced coenzyme $Q_9$, percentage of elimination: 48%) (isolated product yield: 93 mol %). The reduced coenzyme $Q_{10}$/oxidized coenzyme $Q_{10}$ weight ratio of the crystals obtained was 99.2/0.8, and the purity of the reduced coenzyme $Q_{10}$ was 98.9%.

EXAMPLE 4

The reduction reaction was carried out under the same condition as in Example 1, and further solvent substitution was carried out to prepare a 7% (w/w) ethanol solution at 50° C. (containing 100 g of reduced coenzyme $Q_{10}$ (containing 0.40% of reduced coenzyme $Q_9$)). This ethanol solution was added with 50 g of water and cooled to 2° C. at cooling rate of 10° C./hour while stirring in a nitrogen atmosphere to precipitate a crystal. The slurry showed good fluidity and was easily brushed away from a crystallization container. All the above operations were carried out in a nitrogen atmosphere. The obtained slurry was filtered under reduced pressure (filterability was excellent as compared with Example 1), and the wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to obtain 97 g of white dry crystals (containing 0.21% of reduced coenzyme $Q_9$, percentage of elimination: 48%) (isolated product yield: 97 mol%). The reduced coenzyme $Q_{10}$/oxidized coenzyme $Q_{10}$ weight ratio of the crystals obtained was 99.2/0.8, and the purity of the reduced coenzyme $Q_{10}$ was 98.9%.

EXAMPLE 5

Oxidized coenzyme $Q_{10}$ (100 g; purity 99.4%) was dissolved in 1000 g of ethyl acetate at 25° C. While stirring (power required for stirring 0.3 kW/m$^3$), an aqueous solution prepared by dissolving 100 g of sodium hyposulfite (purity: at least 75%) in 1000 ml of water was gradually added as a reducing agent to carry out the reduction reaction at 25° C. and at pH of 4 to 6. After the lapse of 2 hours, an aqueous phase was removed from the reaction solution, and an ethyl acetate phase was washed with 1000 g of deaerated saturated brine for 6 times. This ethyl acetate phase was concentrated at 48° C. from 1100 g to 300 g under reduced pressure, and 1100 g of ethanol and 50 g of water were added while maintaining this temperature in a nitrogen atmosphere. After that, the mixture was cooled to 2° C. at cooling rate of 10° C./hour while stirring (power required for stirring 0.3 kW/m$^3$) to precipitate a crystal. The slurry showed good fluidity and was easily brushed away from a crystallization container. The obtained slurry was filtered under reduced pressure (filterability was excellent as compared with Example 1). The wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to obtain 91 g of white dry crystals (isolated product yield: 91 mol %). The reduced coenzyme $Q_{10}$/oxidized coenzyme $Q_{10}$ weight ratio of the crystals obtained was 99.1/0.9, and the purity of the reduced coenzyme $Q_{10}$ was 98.8%.

EXAMPLE 6

Oxidized coenzyme $Q_{10}$ (100 g; purity 99.4%) was dissolved in 1000 g of heptane at 25° C. To this mixture, 1100 g of 2.9 N sulfuric acid and 15 g of zinc powder were added, and the reduction reaction was carried out at 25° C. for 6 hours while stirring (power required for stirring 0.3 kW/m$^3$). After adding 1000 g of concentrated hydrochloric acid, an aqueous phase was removed from the reaction solution and a heptane phase was washed with 1000 g of deaerated saturated brine for 6 times. All the above operations were carried out in a nitrogen atmosphere. This heptane phase was subjected to solvent substitution under reduced pressure to prepare a 7% (w/w) ethanol solution of reduced coenzyme $Q_{10}$ at 50° C. Moreover, the solution was cooled to 2° C. at cooling rate of 10° C./hour while stirring in a nitrogen atmosphere (power required for stirring 0.3 kW/m$^3$) to precipitate a crystal. The slurry showed good fluidity and was easily brushed away from a crystallization container. The obtained slurry was filtered under reduced pressure (filterability was good same as in Example 1), and the wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to obtain 95 g of white dry crystals (isolated product yield: 95 mol %). The reduced coenzyme $Q_{10}$/oxidized coenzyme $Q_{10}$ weight ratio of the crystals obtained was 99.3/0.7, and the purity of the reduced coenzyme $Q_{10}$ was 99.0%.

COMPARATIVE EXAMPLE 1

A heptane phase (containing 0.40% of reduced coenzyme $Q_9$, purity 99.4%) containing 100 g of reduced coenzyme $Q_{10}$ washed with saturated brine was obtained in the same manner as Example 1. This heptane phase was cooled from 50° C. to 2° C. at cooling rate of 10° C./hour while stirring (power required for stirring 0.3 kW/m$^3$) to precipitate a crystal. The obtained slurry showed poor fluidity and was difficult to brush away from a crystallization container as compared with Example 1. All the above operations were carried out in a nitrogen atmosphere. The obtained slurry was filtered under reduced pressure, and the wet crystals were washed in sequence with cold heptane, cold ethanol, cold water, cold ethanol and cold heptane (the cold solvents used for washing having a temperature of 2° C.). Furthermore, the wet crystal was dried under reduced pressure (20-40° C., 1-30 mmHg) to obtain 93 g of white dry crystals (containing 0.29% of reduced coenzyme $Q_9$, percentage of elimination: 28%) (isolated product yield: 93 mol %). The reduced coenzyme $Q_{10}$/oxidized coenzyme $Q_{10}$ weight ratio of the crystals obtained was 99.6/0.4, and the purity of the reduced coenzyme $Q_{10}$ was 99.2%. The slurry was filtered using a 20 cm-diameter Nutsche funnel with a filter spread thereon and depressurized by an aspirator. The time required for filtration was 37 minutes. Moreover, the obtained crystals were observed with an optical microscope together with the crystals obtained in Examples 1 to 6, they were needle crystals obviously smaller than the cases of Examples 1 to 6.

EXAMPLE 7

Oxidized coenzyme $Q_{10}$ (100 g; purity 99.4%) was dissolved in 1000 g of hexane at 25° C. While stirring (power required for stirring 0.3 kW/m$^3$), an aqueous solution prepared by dissolving 40 g of sodium hyposulfite (purity: at least 75%) in 1000 ml of water was gradually added as a reducing agent to carry out the reduction reaction at 25° C. and pH range of 4 to 6. After the lapse of 2 hours, an aqueous phase was removed from the reaction solution, and a hexane phase was washed with 1000 g of deaerated saturated brine for 6 times. All the above operations were carried out in a nitrogen atmosphere. This hexane phase was subjected to solvent substitution under reduced pressure to prepare a 7% (w/w) ethanol solution of reduced coenzyme $Q_{10}$ at 50° C. Moreover, the solution was cooled to 2° C. at cooling rate of 10° C./hour while stirring in a nitrogen atmosphere (power required for stirring 0.3 kW/m$^3$) to precipitate a crystal. The slurry showed good fluidity and was easily brushed away from a crystallization container. The obtained slurry was filtered under reduced pressure, and the wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to give 95 g of white dry crystals (isolated product yield: 95 mol %). The reduced coenzyme $Q_{10}$/oxidized coenzyme $Q_{10}$ weight ratio of the crystals obtained was 99.2/0.8, and the purity of the reduced coenzyme $Q_{10}$ was 98.9%.

EXAMPLE 8

A 7% (w/w) ethanol solution of reduced coenzyme $Q_{10}$ at 50° C. was prepared (containing 1.00% of reduced coenzyme $Q_9$, 0.30% of reduced coenzyme $Q_8$ and 0.04% of reduced coenzyme $Q_7$) in the same manner as in Example 1 except that the purity of oxidized coenzyme $Q_8$ used was 98.4% (containing 1.0% of oxidized coenzyme $Q_9$, 0.30% of oxidized coenzyme $Q_8$ and 0.04% of oxidized coenzyme $Q_7$). This ethanol solution was added with 50 g of water and cooled to 2 ° C. at cooling rate of 3° C./hour while stirring (power required for stirring 0.3 kW/m$^3$) to precipitate a crystal. The slurry showed fairly good fluidity and was easily brushed away from a crystallization container. All the above operations were carried out in a nitrogen atmosphere. The obtained slurry was filtered under reduced pressure (filterability was excellent as compared with Example 1), and the wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to give 95 g of white dry crystals (containing 0.52% of reduced coenzyme $Q_9$, removal rate was 48%; reduced coenzyme Q8 and reduced coenzyme Q7 were not detected) (yield: 97 mol %). The reduced coenzyme $Q_{10}$/oxidized coenzyme $Q_{10}$ weight ratio of the crystals obtained was 99.3/0.7, and the purity of the reduced coenzyme $Q_{10}$ was 98.7%.

EXAMPLE 9

To 1000 g of ethanol, oxidized coenzyme $Q_{10}$ (100 g; purity 99.4%) and 60 g of L-ascorbic acid were added, and the mixture solution was stirred at 78° C. to carry out the reduction reaction. After the lapse of 30 hours, the solution was cooled to 50° C. and added with 400 g of ethanol while maintaining this temperature . While stirring (power required for stirring 0.3 kW/m$^3$), this ethanol solution was cooled to 2° C. at cooling rate of 10° C./hour to give white slurry. The slurry showed good fluidity and was easily brushed away from a crystallization container. The obtained slurry was filtered under reduced pressure (filterability was good same as in Example 1), the wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to give 95 g of white dry crystals (isolated product yield: 95 mol %). All the above operations were carried out in a nitrogen atmosphere. The reduced coenzyme $Q_{10}$/oxidized coenzyme $Q_{10}$ weight ratio of the crystals obtained was 99.5/0.5, and the purity of the reduced coenzyme $Q_{10}$ was 99.2%.

EXAMPLE 10

Oxidized coenzyme $Q_{10}$ (100 g; 99.4% of purity) and 60 g of L-ascorbic acid were added to 1000 g of ethanol, the mixture was stirred at 78° C. and subjected to the reduction reaction. After the lapse of 30 hours, the mixture was cooled to 50° C. and added with 330 g of ethanol and 70 g of water while maintaining this temperature. This ethanol solution was cooled to 2° C. at cooling rate of 10° C./hour while stirring (power required for stirring 0.3 kW/m$^3$) to give white slurry. The slurry showed fairly good fluidity and was easily brushed away from a crystallization container. The obtained slurry was filtered under reduced pressure (filterability was excellent as compared with example 1) The wet crystals were washed in sequence with cold ethanol, cold water and cold ethanol (the cold solvents used for washing having a temperature of 2° C.). Furthermore, the wet crystal was dried under reduced pressure (20-40° C., 1-30 mmHg) to give 97 g of white dry crystals (isolated product yield: 97 mol %). All the above operations were carried out in a nitrogen atmosphere. The reduced coenzyme $Q_{10}$/oxidized coenzyme $Q_{10}$ weight ratio of the crystals obtained was 99.5/0.5, and the purity of the reduced coenzyme $Q_{10}$ was 99.2%.

EXAMPLE 11

To 1000 g of acetone, oxidized coenzyme $Q_{10}$ (100 g; purity 99.4%), 60 g of L-ascorbic acid and 30 g of sodium bicarbonate were added, and the mixture solution was stirred at 50° C. to carry out the reduction reaction. After the lapse of 45 hours, 400 g of acetone was added while maintaining this temperature. While stirring (power required for stirring 0.3 kW/m$^3$), this acetone solution was cooled to 2° C. at cooling rate of 10° C./hour to give white slurry. The slurry showed good fluidity and was easily brushed away from a crystallization container. The obtained slurry was filtered under reduced pressure (filterability was good same as Example 1). The wet crystals were washed in sequence with cold acetone, cold water and cold acetone (the cold solvents used for washing having a temperature of 2° C.). Furthermore, the wet crystal was dried under reduced pressure (20-40° C., 1-30 mmHg) to give 93 g of white dry crystals (isolated product yield: 93 mol %). All the above operations were carried out in a nitrogen atmosphere. The reduced coenzyme $Q_{10}$/oxidized coenzyme $Q_{10}$ weight ratio of the crystals obtained was 99.5/0.5, and the purity of the reduced coenzyme $Q_{10}$ was 99.2%.

REFERENCE EXAMPLE 1

Reduced coenzyme $Q_{10}$ (1 g; the reduced coenzyme $Q_{10}$/oxidized coenzyme $Q_{10}$ weight ratio was 99.6/0.4) was dissolved in 20 g of various solvents shown in Table 1 at 25° C. In the atmosphere, the weight ratio of reduced coenzyme $Q_{10}$/oxidized coenzyme $Q_{10}$ in the solutions was measured after stirring at 25° C. for 24 hours. The results are shown in Table 1.

TABLE 1

| Solvent | R |
| --- | --- |
| Heptane | 99.1/0.9 |
| Hexane | 98.7/1.3 |
| Toluene | 98.8/1.2 |
| Chloroform | 98.9/1.1 |
| Ethyl acetate | 98.9/1.1 |
| Methyl tert-butyl ether | 98.6/1.4 |
| Tetrahydrofuran | 98.5/1.5 |

R: Reduced coenzyme $Q_{10}$/Oxidized coenzyme $Q_{10}$ weight ratio

REFERENCE EXAMPLE 2

Reduced coenzyme $Q_{10}$ (1 g; the reduced coenzyme $Q_{10}$/oxidized coenzyme $Q_{10}$ weight ratio was 99.6/0.4) was dissolved in 100 g of various solvents shown in Table 2 at 35° C. In the atmosphere, the reduced coenzyme $Q_{10}$/oxidized coenzyme $Q_{10}$ weight ratio in the solutions was measured after stirring at 35° C. for 24 hours. The results are shown in Table 2.

TABLE 2

| Solvent | R |
| --- | --- |
| Heptane | 96.7/3.3 |
| Ethyl acetate | 96.4/3.6 |
| Acetonitrile | 96.0/4.0 |

R: Reduced coenzyme $Q_{10}$/Oxidized coenzyme $Q_{10}$ weight ratio

Industrial Applicability

The present invention, which has the constitution described above, makes it possible to obtain a high-quality reduced coenzyme $Q_{10}$ crystal in a convenient and efficient manner by a method excellent in workability and economical efficiency.

What is claimed is:

1. A method of producing reduced coenzyme $Q_{10}$ crystals which comprises;
   (a) obtaining a solution of the reduced coenzyme $Q_{10}$ by reducing oxidized coenzyme $Q_{10}$ into the reduced coenzyme $Q_{10}$ in a solution of an alcohol and/or a ketone wherein the ratio of the alcohol and/or the ketone in a solvent is at least 80 w/w %; and
   (b) crystallizing reduced coenzyme $Q_{10}$ directly from the solution of the alcohol and/or the ketone by cooling or by a combination of crystallization by cooling with another method of crystallization.

2. The method according to claim 1, wherein reduced coenzyme $Q_{10}$ is crystallized in a solution of an alcohol containing reduced coenzyme $Q_{10}$ is obtained by reducing oxidized coenzyme $Q_{10}$ into reduced coenzyme $Q_{10}$ in an alcohol solution.

3. The method according to claim 1, wherein the alcohol is a monohydric alcohol containing 1 to 20 carbon atoms.

4. The method according to claim 1, wherein the alcohol is a monohydric alcohol containing 1 to 5 carbon atoms.

5. The method according to claim 4, wherein the monohydric alcohol containing 1 to 5 carbon atoms is ethanol.

6. The method according to claim 1, wherein reduced coenzyme $Q_{10}$ is crystallized from a solution of a ketone containing reduced coenzyme $Q_{10}$ is obtained by reducing oxidized coenzyme $Q_{10}$ into reduced coenzyme $Q_{10}$ in a ketone solution.

7. The method according to claim 1, wherein the ketone is a ketone containing 3 to 6 carbon atoms.

8. The method according to claim 7, wherein the ketone containing 3 to 6 carbon atoms is acetone.

9. The method according to claim 1, wherein ascorbic acid or a related compound thereof is used as a reducing agent.

10. The method according to claim 9, wherein the reduction is carried out in the presence of a basic substance or a hydrogensulfite salt.

11. The method according to claim 1, wherein the concentration of reduced coenzyme $Q_{10}$ in the solution of the alcohol and/or ketone at the time of completion of crystallization is not lower than 2 w/w % and not higher than 10 w/w %.

12. The method according to claim 1, wherein the crystallization is carried out under forced flowing caused by a power required for stirring per unit volume of not weaker than 0.01 kW/m$^3$.

13. The method according to claim 12, wherein the concentration of reduced coenzyme $Q_{10}$ in the solution of the alcohol and/or the ketone at the time of completion of crystallization is not lower than 1 w/w % and not higher than 15 w/w %.

14. The method according to claim 13, wherein the crystallization is carried with simultaneous removal of impurities.

15. The method according to claim 1, wherein the concentration of reduced coenzyme $Q_{10}$ in the solution of the alcohol and/or the ketone at the time of completion of crystallization is not lower than 1 w/w % and not higher than 15 w/w %.

* * * * *